(12) United States Patent
Jo et al.

(10) Patent No.: US 9,696,144 B2
(45) Date of Patent: Jul. 4, 2017

(54) THREE-DIMENSIONAL SHAPE MEASURING DEVICE CAPABLE OF MEASURING COLOR INFORMATION

(71) Applicant: SNU Precision Co., Ltd., Chungcheongnam-do (KR)

(72) Inventors: Tae Yong Jo, Seoul (KR); Young Min Hwang, Seoul (KR); Seong Ryong Kim, Seoul (KR); Sang Soo Kang, Incheon (KR); Heui Jae Pahk, Seoul (KR)

(73) Assignee: SNU PRECISION CO., LTD., Chungcheongnam-Do (KR)

( * ) Notice: Subject to any disclaimer, the term of this patent is extended or adjusted under 35 U.S.C. 154(b) by 0 days.

(21) Appl. No.: 14/777,653

(22) PCT Filed: Mar. 17, 2014

(86) PCT No.: PCT/KR2014/002217
§ 371 (c)(1),
(2) Date: Sep. 16, 2015

(87) PCT Pub. No.: WO2014/148781
PCT Pub. Date: Sep. 25, 2014

(65) Prior Publication Data
US 2016/0102970 A1   Apr. 14, 2016

(30) Foreign Application Priority Data
Mar. 18, 2013 (KR) .................. 10-2013-0028630

(51) Int. Cl.
*G01B 11/24* (2006.01)
*G01B 9/02* (2006.01)
(Continued)

(52) U.S. Cl.
CPC ...... *G01B 11/2441* (2013.01); *G01B 9/02029* (2013.01); *G01B 9/02034* (2013.01);
(Continued)

(58) Field of Classification Search
CPC ............ G01B 11/2441; G01B 9/02057; G01B 9/02059; G01B 2290/50
See application file for complete search history.

(56) References Cited

U.S. PATENT DOCUMENTS

2005/0206850 A1* 9/2005 Shimizu ................. G03B 21/18
353/55
2010/0128276 A1* 5/2010 De Groot ........... G01B 11/2441
356/450
(Continued)

FOREIGN PATENT DOCUMENTS

KR        10-0672818 B1     1/2007
KR    10-2009-0063874 A     6/2009
(Continued)

OTHER PUBLICATIONS

International Search Report in International Application No. PCT/KR2014/002217, filed Mar. 17, 2014.

*Primary Examiner* — Jonathan Hansen
(74) *Attorney, Agent, or Firm* — Saliwanchik, Lloyd & Eisenschenk

(57) ABSTRACT

Provided herein is a three-dimensional shape measurement apparatus capable of measuring a shape of a measurement object using an interferometer and color information of the measurement object, the apparatus including a light source for emitting a light; a light divider for reflecting the light emitted from the light source or transmitting a light reflected by the measurement object; a lens unit for focusing the light reflected by the light divider onto the measurement object; a light detector for detecting the light reflected from the measurement object; and a light adjuster arranged on a light (Continued)

path between the light source and the light divider, and configured to interrupt the light being emitted from a central area of the light source to reduce interference of light occurring in the lens unit.

3 Claims, 7 Drawing Sheets

(51) Int. Cl.
- *G01N 21/88* (2006.01)
- *G01N 21/95* (2006.01)
- *G01J 3/50* (2006.01)
- *G01J 3/02* (2006.01)

(52) U.S. Cl.
CPC ........ *G01B 9/02057* (2013.01); *G01J 3/0208* (2013.01); *G01J 3/0229* (2013.01); *G01J 3/50* (2013.01); *G01J 3/506* (2013.01); *G01N 21/8806* (2013.01); *G01N 21/95* (2013.01); *G01N 2021/8845* (2013.01); *G01N 2021/9513* (2013.01)

(56) References Cited

U.S. PATENT DOCUMENTS

| | | | |
|---|---|---|---|
| 2012/0038910 A1* | 2/2012 | Stevens | G01N 21/95623 356/237.2 |
| 2016/0091422 A1* | 3/2016 | Van Der Zouw | G01N 21/4738 356/445 |

FOREIGN PATENT DOCUMENTS

| | | |
|---|---|---|
| KR | 10-2011-0086222 A | 7/2011 |
| WO | WO-2014126778 A3 | 8/2014 |

\* cited by examiner

[Fig. 1]
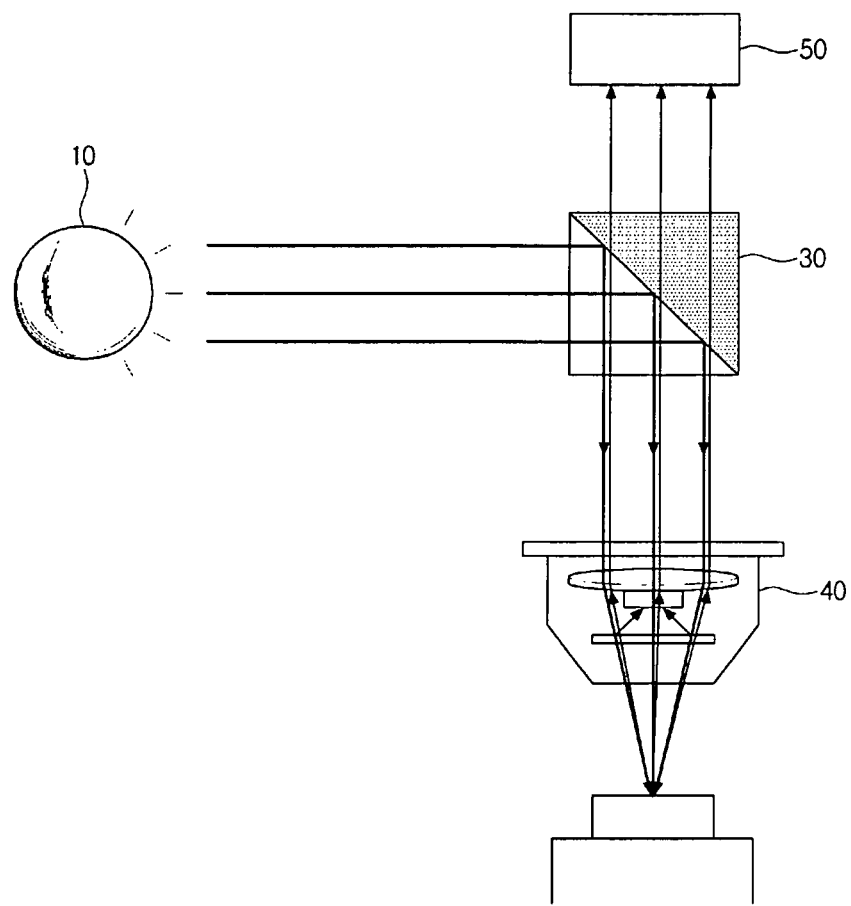

[Fig. 2]
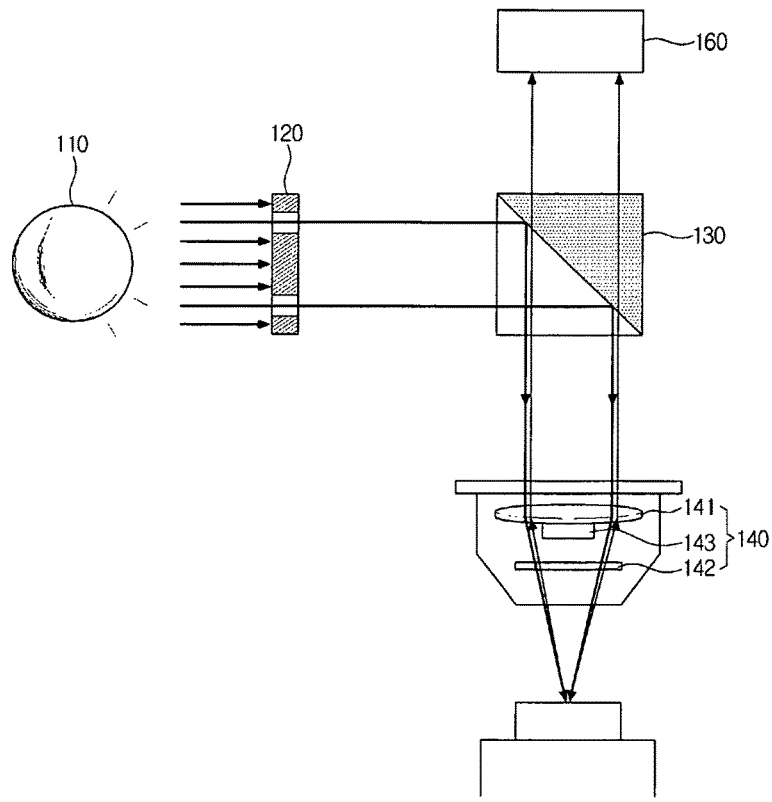
[Fig. 3]
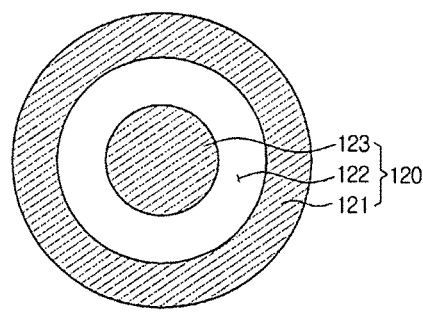
[Fig. 4]
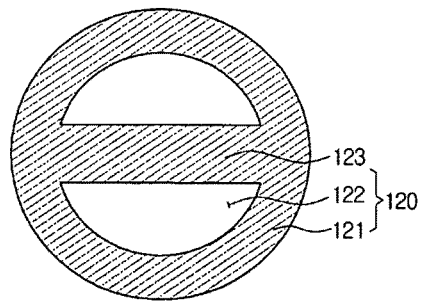

[Fig.7]
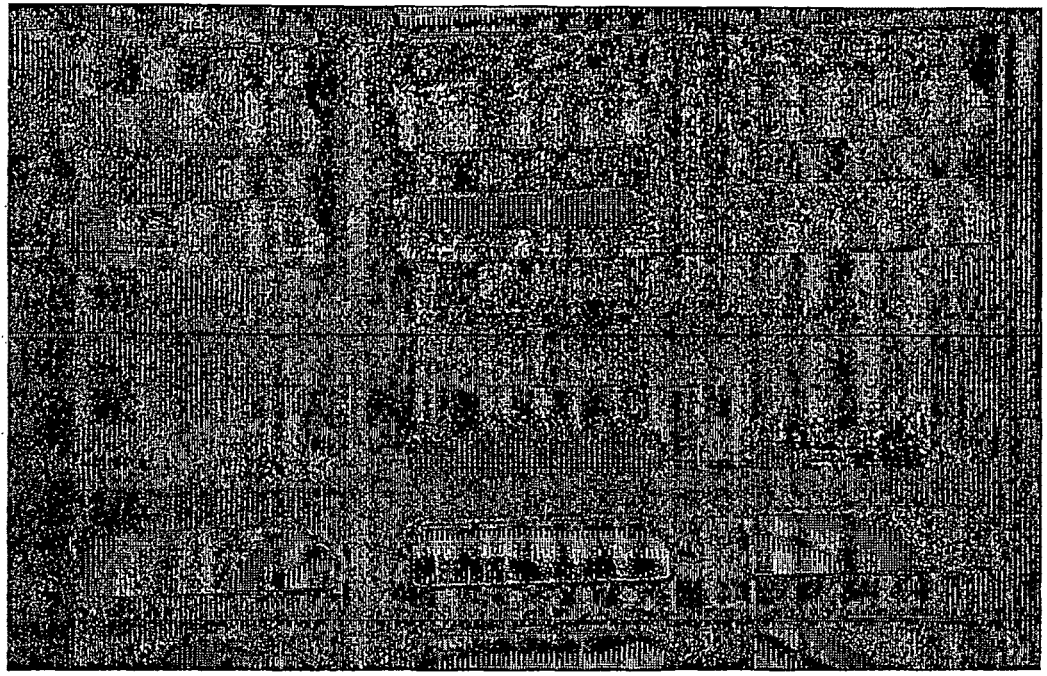
[Fig.8]
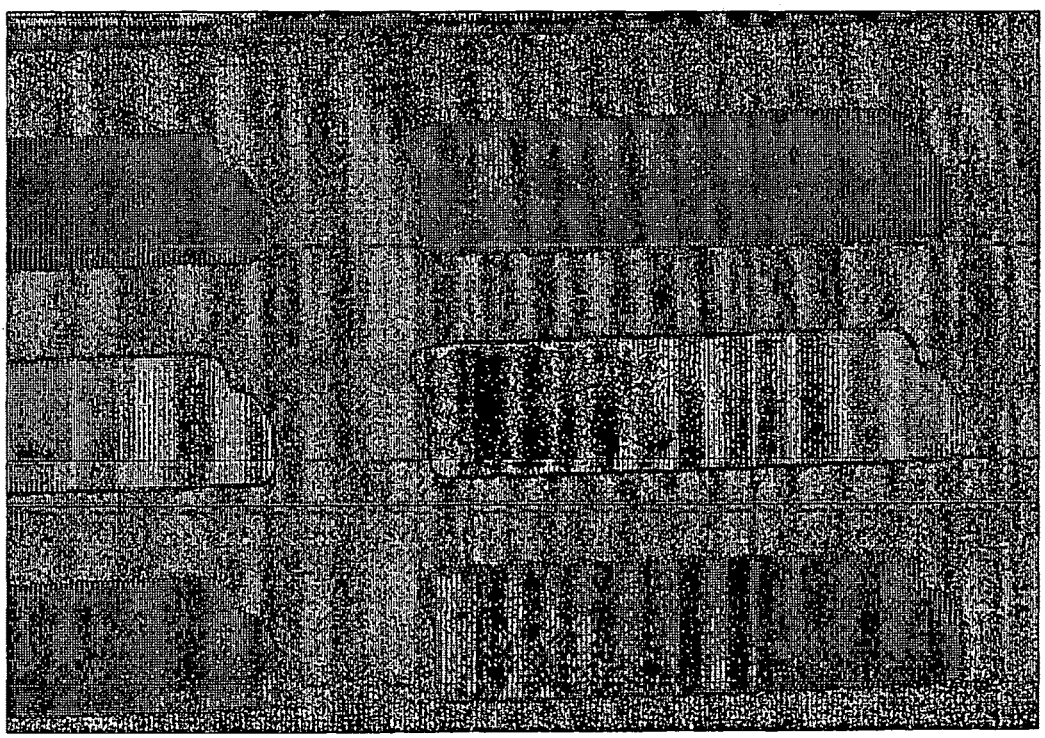

[Fig. 9]
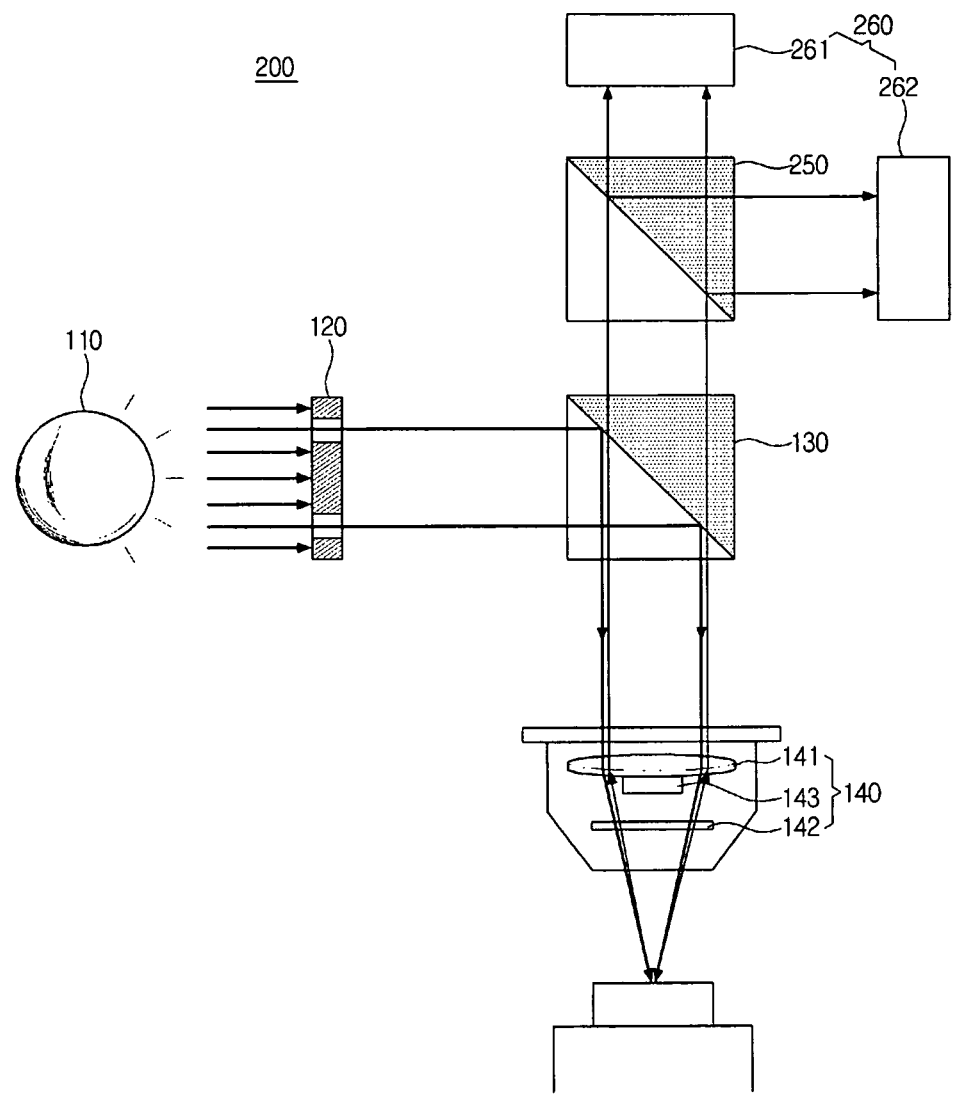

THREE-DIMENSIONAL SHAPE MEASURING DEVICE CAPABLE OF MEASURING COLOR INFORMATION

CROSS-REFERENCE TO RELATED APPLICATIONS

This application is the U.S. national stage application of International Patent Application No. PCT/KR2014/002217, filed Mar. 17, 2014, which claims priority to Korean Application No. 10-2013-0028630, filed Mar. 18, 2013, the disclosures of each of which are incorporated herein by reference in their entirety.

TECHNICAL FIELD

The invention relates to a three-dimensional shape measurement apparatus capable of measuring color information, and more particularly, to a three-dimensional shape measurement apparatus capable of measuring color information of a certain measurement object while using an interferometer.

BACKGROUND

Controlling the thickness of a thin film layer takes a large part in determining quality in a semiconductor process and FPD process, and thus it is essential to directly monitor the thin film layer during the process. A 'thin film layer' is a base layer having a very thin thickness formed on a surface of a substrate, the thickness being generally between several nm and several µm. In order to apply such a thin film layer to certain uses, it is necessary to know the thickness, composition, illumination and other physical and optical characteristics of the thin film layer. Herein, there are various methods for measuring a thickness of a thin film layer to be used in a semiconductor process and other application processes, but the most general methods are those using an interferometer or a spectrophotometer.

Meanwhile, for semiconductor devices such as a LCD panel having color information such as R/G/B, recently a lot of interest is being paid to a technology for measuring color information such as R/G/B at the same time of measuring physical and optical characteristics of the thin film layer.

FIG. 1 is a right path view schematically illustrating a conventional three-dimensional shape measurement apparatus. According to FIG. 1, a conventional three-dimensional shape measurement apparatus includes a light source 10, light divider 30, lens unit 40, and light detector 50. The conventional three-dimensional shape measurement apparatus measures a shape of a certain object by observing the interference phenomenon that occurs as a light is divided into two or more light streams at the lens unit 40, generating a difference in proceeding paths, and then the divided lights are combined again.

However, such a conventional three-dimensional shape measurement apparatus cannot measure the exact color information of a certain object due to the interference effect of light, and thus it is general to identify a shape of the certain object based on the patterns formed differently per color on the measurement object.

That is, the conventional technology does not directly identify the measurement object differently per color information, and thus there occurs a problem that in a case where a pattern is not formed on the measurement object or where a pattern is formed identically per color, it is not possible to make a measurement differently per color information.

SUMMARY

Problems to be Solved

A purpose of the present disclosure is to resolve the aforementioned problems of prior art, that is to provide a three-dimensional shape measurement apparatus capable of measuring a shape of a certain object using an interferometer, and additionally capable of measuring color information of the measurement object.

Technical Solutions

The purpose of the invention is achieved by a three-dimensional shape measurement apparatus for measuring a shape of a measurement object using an interference light, the apparatus including a light source for emitting a light; a light divider for reflecting the light emitted from the light source or transmitting a light reflected by the measurement object; a lens unit for focusing the light reflected by the light divider onto the measurement object; a light detector for detecting the light reflected from the measurement object; and a light adjuster arranged on a light path between the light source and the light divider and configured to interrupt the light being emitted from a central area of the light source to reduce interference of light occurring in the lens unit.

Herein, the light adjuster may include a main body provided with a transmitter for transmitting light; and a light diaphragm arranged inside the transmitter and configured to interrupt light, and the light path where the light emitted from the light source penetrates may be limited to an area between an exterior surface of the transmitter and an exterior surface of the light diaphragm.

Furthermore, the light diaphragm may be formed to have at least one of a circular, a polygonal and a rod shape.

Herein, the light adjuster may be selectively mounted on the light path between the light source and the light divider.

Furthermore, the apparatus may further include a subsidiary light adjuster arranged on the light path between the light adjuster and light divider and configured to interrupt a part of the light that penetrated the light adjuster.

Herein, a magnification ratio of the lens unit may be or less than 50 times.

Furthermore, the subsidiary light adjuster may be provided with an aperture for transmitting light, and a part of the light that penetrated the light adjuster may penetrate the aperture and reach the measurement object.

Herein, a central axis of the light diaphragm and a central axis of the aperture may be arranged to be the same.

Furthermore, a size area of the transmitter may be larger than a size area of the aperture.

Herein, the light detector may include a first camera to be used in measuring the interference of light and a second camera to be used in measuring color information, and the apparatus may further include a second light divider arranged on a light path between the light detector and the light divider and configured to transmit the light reflected from the measurement object to at least one of the first camera and the second camera.

Acting Effects

According to the aforementioned various embodiments of the present disclosure, there is provided a three-dimensional shape measurement apparatus capable of measuring a shape of a certain object using an interferometer, and also capable of measuring color information of the certain object.

Furthermore, as a light adjuster is selectively mounted, it is possible to measure both the shape and color information of the measurement object.

Furthermore, it is possible to adjust the light entering the certain object according to a magnification ratio of the lens unit, thereby measuring color information of the certain object regardless of the magnification ratio of the lens unit.

Furthermore, it is possible to match the central axis of the light diaphragm to the central axis of the aperture, thereby easily adjusting a light entering the certain object.

BRIEF DESCRIPTION OF THE DRAWINGS

FIG. 1 is a light path view schematically illustrating a conventional three-dimensional shape measurement apparatus;

FIG. 2 is a light path view schematically illustrating a three-dimensional shape measurement apparatus capable of measuring color information according to a first embodiment of the present disclosure;

FIG. 3 is a view schematically illustrating an example of a light adjuster of a three-dimensional shape measurement apparatus capable of measuring color information of FIG. 2;

FIG. 4 is a view schematically illustrating another example of a light adjuster of a three-dimensional shape measurement apparatus capable of measuring color information of FIG. 2;

FIG. 7 and FIG. 8 are photographs of color information of a certain measurement object measured in a three-dimensional shape measurement apparatus capable of measuring color information of FIG. 2;

FIG. 9 is a light path view schematically illustrating a three-dimensional shape measurement apparatus capable of measuring color information according to a second embodiment of the present disclosure;

DETAILED DESCRIPTION

Figure 5:
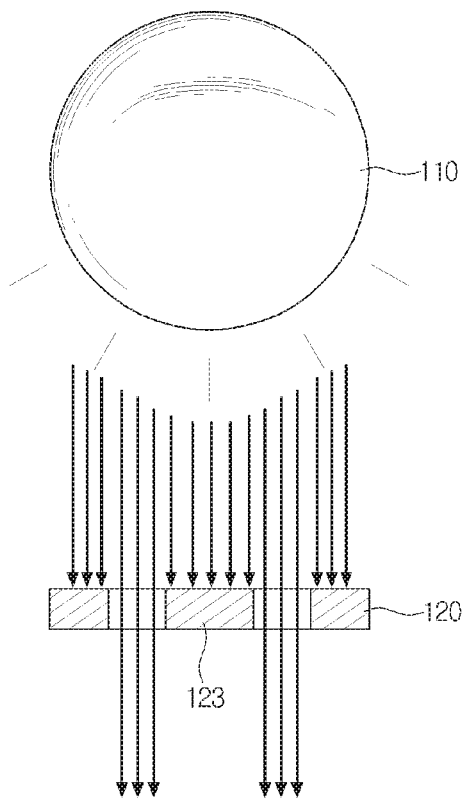
FIG. 5 is a view schematically illustrating a light emitted from a light source of a three-dimensional shape measurement apparatus capable of measuring color information of FIG. 2 penetrating a light adjuster.

In explaining the various embodiments, the various embodiments will be explained using same reference numerals for components with the same configurations, a first embodiment will be explained representatively and the other embodiments will be explained with the main focus on configurations different from those of the first embodiment.

Hereinafter, a three-dimensional shape measurement apparatus capable of measuring color information according to a first embodiment of the present disclosure will be explained in detail with reference to the drawings attached.

FIG. 2 is a light path view schematically illustrating a three-dimensional shape measurement apparatus capable of measuring color information according to the first embodiment of the present disclosure.

Referring to FIG. 2, the three-dimensional shape measurement apparatus capable of measuring color information according to the first embodiment of the present disclosure 100 is configured to minimize an interference effect of light which penetrates a lens unit 140. The three-dimensional shape measurement apparatus 100 includes a light source 110, a light adjuster 120, a light divider 130, a lens unit 140, and a light detector 160.

The light source 110 is for emitting a light, and in the three-dimensional shape measurement apparatus capable of measuring color information according to the first embodiment of the present disclosure 100, the light source 110 is a white color light source, but not limited to the white color light source.

FIG. 3 is a view schematically illustrating an example of a light adjuster of a three-dimensional shape measurement apparatus capable of measuring color information of FIG. 2, and FIG. 4 is a view schematically illustrating another example of a light adjuster of a three-dimensional shape measurement apparatus capable of measuring color information of FIG. 2.

Referring to FIG. 3 or FIG. 4, the light adjuster 120 is arranged on a light path between the light source 110 and a light divider 130 that will be explained hereinafter and the light adjuster 120 minimizes an interference of light in the lens unit 140 that will be explained hereinafter by interrupting the light which is emitted from a central area of the light source 110.

That is, the interference effect of light is used to measure a shape of the certain object, but when measuring color information, the light adjuster 120 is used, thereby preventing a central light where interference occurs actively in the light source 110 from proceeding towards the certain measurement object, so as to minimize the interference of light occurring in the lens unit 130 that will be explained hereinafter and measure color information of the measurement object.

In the three-dimensional shape measurement apparatus 100 capable of measuring color information according to the first embodiment of the present disclosure, the light adjuster 120 includes a main body 121 and a light diaphragm 123.

The main body 121 serves as a main frame of the light adjuster 120, and a transmitter 122 that transmits light is formed on an area that includes the central area of the light source 110.

Herein, the main body 121 and the transmitter 122 have the same central axis, and it is desirable that the transmitter 122 is formed in a central part of the main body 121, but not limited to the central part.

Furthermore, the main body 121 and transmitter 122 are configured to have a circular shape, but not limited to the circular shape, and thus the main body 121 and transmitter 122 may be configured to have a polygonal shape.

Furthermore, the transmitter 122 is configured to penetrate the main body 121, but not limited to this configuration, and thus the transmitter 122 may be made of a film that transmits light.

The light diaphragm 123 is arranged inside the transmitter 122 and the light diaphragm 123 is configured to interrupt a light (hereinafter referred to as 'central light') proceeding to an area corresponding to the area where the light diaphragm 123 is arranged, thereby transmitting only light which surrounds the central light and is not the central light.

Herein, the surrounding light has less occurrence rate of the interference effect of light compared to the central light, and the occurrence of the interference effect of light decreases inside the lens unit 140 as well.

Herein, it is desirable that the light diaphragm 123 is formed in a central part of the transmitter 122, but not limited to this configuration.

Furthermore, it is desirable that the light diaphragm 123 is formed to have at least one of a circular, a polygonal, or a rod shape, but not limited to these shapes.

In other words, the light source 110, the main body 121, the transmitter 122 and the light diaphragm 123 are arranged to have the same central axis, and to interrupt the central light, but not limited to this configuration.

Herein, regarding a light path being guided by the light adjuster 120, a light emitted from the light source 110 is transmitted only through an area where the light diaphragm 123 is not formed in the area where the transmitter 122 is formed and hereinafter, the transmitted light is referred to as 'surrounding light'.

That is, a light (central light) proceeding to an area where the transmitter 122 and light diaphragm 123 overlap is interrupted by the light adjuster 120.

Meanwhile, the light adjuster 120 is arranged to be selectively mounted on the light path between the light source 110 and light divider 130, but not limited to this configuration. That is, according to user's intentions, the light adjuster may transmit only the surrounding light so as to measure color information of the measurement object, or may transmit an entirety of the light being emitted from the light source 110 so as to measure the shape of the measurement object through interference measurement.

The light divider 130 reflects or transmits the light that penetrated the light adjuster 120. In other words, the light divider 130 reflects the light through the light divider 130 so that the light that penetrated the light adjuster 120 enters the measurement object, or transmits the light through the light divider 130 so that the light reflected from the measurement object proceeds towards the light detector 160.

Meanwhile, on the light path between the light adjuster 120 and light divider 130 of the three-dimensional shape measurement apparatus capable of measuring color information according to the first embodiment of the present disclosure 100, a neutral density filter (ND filter, not illustrated) may be provided in order to reduce the brightness while retaining the spectrum characteristics of the light that penetrated the light adjuster 120, but not limited to this configuration.

Furthermore, a light concentrating lens (not illustrated) may be installed in order to focus the light that penetrated the ND filter (not illustrated), and a collimator (not illustrated) may be installed in order to parallelize the light that penetrated the light concentrating lens (not illustrated), but not limited to this configuration.

The lens unit 140 is a component for focusing the light reflected from the light divider 130 to the measurement object, and in the lens unit 140, the light reflected from the light divider 130 is divided into a light that proceeds toward the measurement object and a light that does not proceed toward the measurement object.

Herein, the light that does not proceed toward the measurement object becomes a reference light and the light that proceeds toward the measurement object is reflected by the measurement object, generating a light path difference against the reference light. That is, the light that proceeds toward the measurement object and the light that does not proceed toward the measurement object generates interference, enabling to measure the shape of the measurement object.

In the three-dimensional shape measurement apparatus capable of measuring color information according to the first embodiment of the present disclosure 100, the lens unit 140 is configured as one module consisting of a lens 141 that focuses the light reflected from the light divider 130 onto the measurement object; a reference light divider 142 that transmits the light that penetrated the lens 141 to the measurement object or reflects the light that penetrated the lens to a reference mirror 143 that will be explained hereinafter; and the reference mirror 143 that emits the light reflected from the reference divider 142 and generates the reference light, but not limited to this configuration.

However, in a case where the light adjuster 120 is mounted on the light path between the light source 110 and light divider 130 and only the surrounding light enters the lens unit 140, there is less occurrence rate of the interference effect of light compared to when the central light enters the lens unit 140, and the amount of light being reflected by the reference light divider 142 to the reference mirror 143 decreases significantly, and most of the light proceeds toward the measurement object.

That is, depending on whether or not the light adjuster 120 is mounted on the light path between the light source 110 and the light divider 130, it is possible to select whether to measure the shape of the measurement object using the interference of light or to measure color information of the measurement object by limiting the interference of light.

The light detector 160 is a component for detecting an interference signal generated by the light reflected from the measurement object and the reference light. The light detector 160 detects the interference signal generated by the light reflected by the measurement object and the reference light.

Furthermore, in the three-dimensional shape measurement object capable of measuring color information according to the first embodiment of the present disclosure 100, the light detector 160 uses a charge coupled device (CCD) camera, but not limited to this configuration.

Hereinafter, an operation of the three-dimensional shape measurement apparatus capable of measuring color information aforementioned according to the first embodiment of the present disclosure will be explained with reference to the light path.

Meanwhile, a case where the light adjuster 120 deviates from the light path between the light source 110 and light divider 130 is the same as the principle of the apparatus that measures the shape of the measurement object using the conventional interferometer principle, and thus detailed explanation is omitted herein.

However, in such a case, the light that penetrated the light divider 130 may be transmitted to the light detector 160, thereby enabling measuring the shape of the measurement object and the like.

Hereinafter, regarding the light emitted from the light source 110 through the light adjuster 120, explanation will be made on a case where only the surrounding light enters the measurement object.

Figure 6:
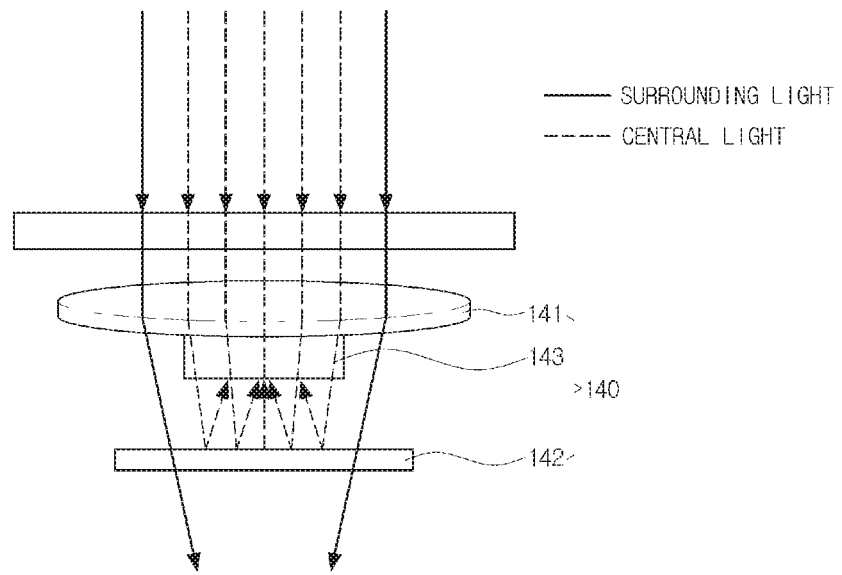
FIG. 6 is a view schematically illustrating a light that penetrated a light adjuster of a three-dimensional shape measurement apparatus capable of measuring color information of FIG. 5 entering a lens unit.

FIG. 5 is a view schematically illustrating a light emitted from the light source of the three-dimensional shape measurement object capable of measuring color information of FIG. 2 penetrating the light adjuster, and FIG. 6 is a view schematically illustrating a light that penetrated the light adjuster of the three-dimensional shape measurement apparatus capable of color information of FIG. 5 entering the lens unit.

Referring to FIG. 5, the light emitted from the light source 110 penetrates the light adjuster 120, and the transmission area of the light is limited to only a partial area between the transmitter 122 and light diaphragm 123 in the light adjuster 120. The partial area between the transmitter 122 and light diaphragm 123 interrupts the central light of the light source 110 as aforementioned, and utilizes the surrounding light having a small interference effect so as to measure the color information of the measurement object.

Only the surrounding light is proceeded by the light adjuster 120, and the light divider 130 reflects the surrounding light that penetrated the light adjuster 120 towards the measurement object.

Referring to FIG. 6, the surrounding light reflected by the light divider 130 enters the lens unit 140, and penetrates the lens 141 first. The surrounding light that penetrated the lens 141 penetrates the reference light divider 142, but since the surrounding light has a small interference effect, the light being divided towards the reference mirror 143 side is minimized, and most of the light, preferably an entirety of the surrounding light is emitted towards the measurement object.

The surrounding light after being emitted towards the measurement object penetrates the light divider 130 and enters the light detector 160, thereby obtaining color information of the measurement object from the light detector 160.

FIGS. 7 and 8 are photographs of color information of the measurement object measured by the three-dimensional shape measurement object capable of measuring color information of FIG. 2.

Referring to FIG. 7, a total of 21 patterns of 3 width direction patterns and 7 length direction patterns have been photographed as one image through the three-dimensional shape measurement apparatus according to the first embodiment of the present disclosure 100. The patterns in the width direction all have the same color, whereas in the length direction, red, blue, green, red, blue, green and red are arranged sequentially. One can see that color information of such a pattern has been photographed very clearly.

Furthermore, referring to FIG. 8, the image of FIG. 7 is enlarged, that is, 2 width direction patterns and 3 length direction patterns have been photographed as one image through the three-dimensional shape measurement apparatus according to the first embodiment of the present disclosure 100. As in FIG. 7, all the patterns in the width direction have the same color, whereas in the length direction, blue, green, and red are arranged sequentially, and one can see that color information of such a pattern has been photographed very clearly. Herein, regarding the pattern of red photographed in the leftmost side, only a very small portion of the pattern of red has been photographed, and thus explanation for the very small portions was omitted herein.

Therefore, referring to FIG. 7 and FIG. 8, one can see that it is possible to measure color information of the measurement object very clearly using only the surrounding light of the light source 110 through the three-dimensional shape measurement apparatus according to the first embodiment of the present disclosure 100.

Next, explanation will be made on a three-dimensional shape measurement apparatus capable of measuring color information according to a second embodiment of the present disclosure 200.

FIG. 9 is a light path view schematically illustrating the three-dimensional shape measurement apparatus capable of measuring color information according to the second embodiment of the present disclosure 200.

Referring to FIG. 9, the three-dimensional shape measurement apparatus capable of measuring color information according to the second embodiment of the present disclosure 200 is for minimizing the interference effect of the light penetrating the lens unit 140. The three-dimensional shape measurement apparatus capable of measuring color information according to the second embodiment of the present disclosure 200 includes a light source 110, a light adjuster 120, a light divider 130, a lens unit 140, a second light divider 250, and a light detector 260.

Meanwhile, configurations of the light source 110, the light adjuster 120, the light divider 130, and the lens unit 130 are the same as those of the three-dimensional shape measurement apparatus capable of measuring color information according to the first embodiment of the present disclosure 100, and thus detailed explanation is omitted herein.

The second light divider 250 is a component that divides the light reflected from the measurement object in order to transmit the light to any one of light detectors 260 that will be explained hereinafter, or to all the light detectors 260.

The light detector 260 is a component that detects the light reflected from the measurement object, and according to the second embodiment of the present disclosure, the light detector 260 includes a first camera 261 to be used in interference measurement using an interference light, and a second camera 262 to be used in measuring color information, but not limited to this configuration.

Herein, in a case where the apparatus is used as a general three-dimensional shape measurement apparatus, the light adjuster 120 deviates from the light path, and the light that penetrated the second light divider 250 enters the first camera 261.

Furthermore, when measuring color information, the light adjuster 120 is mounted on the light path, and the light that penetrated the second light divider 250 enters the second camera 262.

Herein, the first camera 261 is configured as a mono camera, and the second camera 262 is configured as a color camera so as to measure color information of the measurement object, but not limited to this configuration.

Hereinafter, explanation will be made on an operation of the three-dimensional shape measurement apparatus capable of measuring color information according to the second embodiment of the present disclosure.

The process of the light emitted from the light source 110 being reflected from the measurement object is the same as in the three-dimensional shape measurement apparatus capable of measuring color information according to the first embodiment of the present disclosure 100, and thus detailed explanation is omitted herein.

The light reflected from the measurement object penetrates the light divider 130 and enters the second light divider 250. Depending on whether or not the light adjuster 120 is mounted on the light path, in other words, depending on whether the three-dimensional shape measurement apparatus capable of measuring color information according to the second embodiment of the present disclosure will measure the shape or the color information of the measurement object, the proceeding direction of the light transmitted from the second light divider 250 will be determined.

That is, in a case of measuring a shape of the measurement object, the light that penetrated the second light divider 250 is transmitted to the first camera 261 so that the shape of the measurement object may be observed through the first camera 261, whereas in a case of measuring color information of the measurement object, the light that penetrated the second light divider 250 is transmitted to the second camera 262 so that the color information of the measurement object may be observed through the second camera 262.

Next, explanation will be made on a three-dimensional shape measurement apparatus capable of measuring color information according to a third embodiment of the present disclosure.

Figure 10:
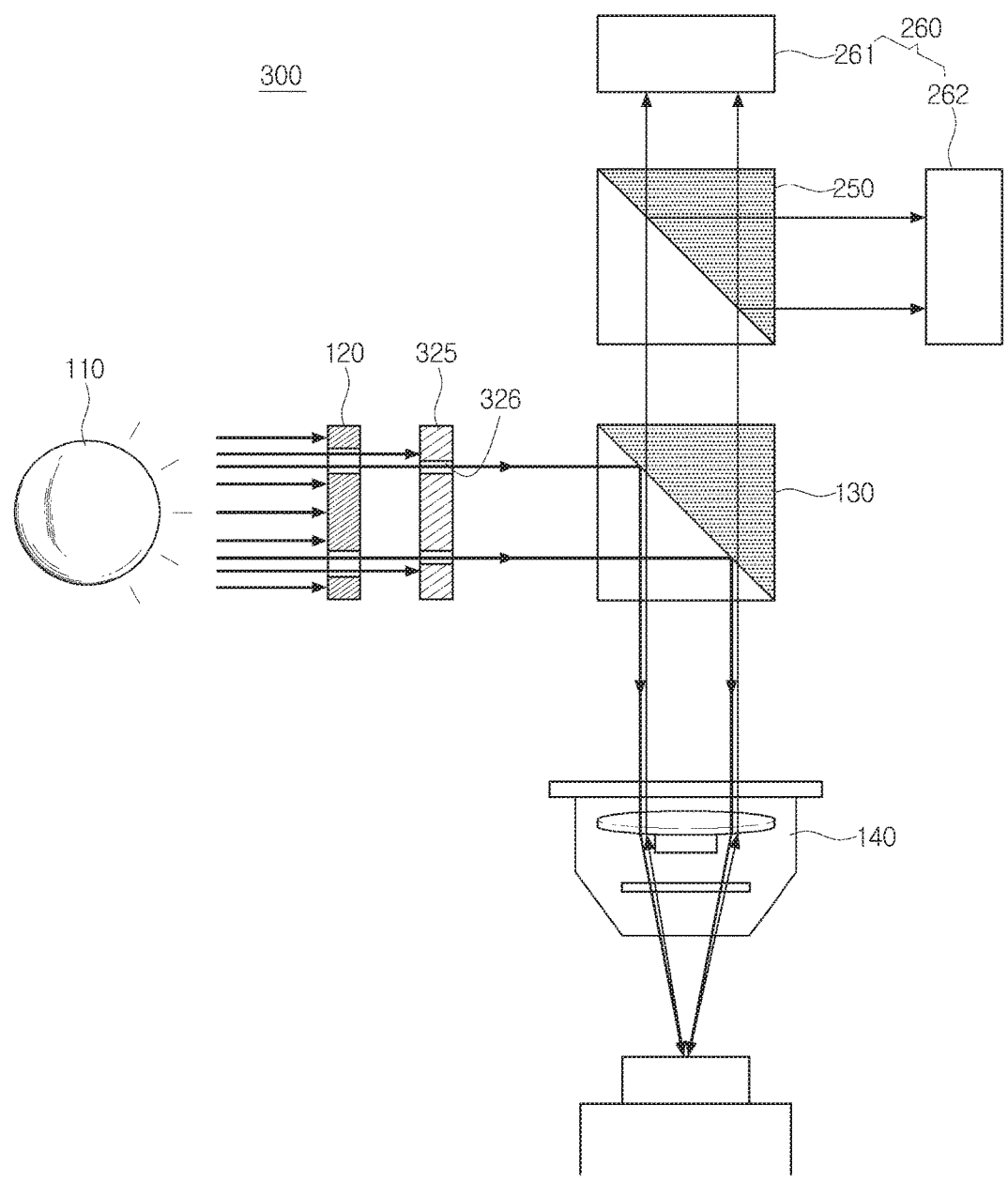
FIG. 10 is a light path view schematically illustrating a three-dimensional shape measurement apparatus capable of measuring color information according a second embodiment of the present disclosure.
Figure 11:
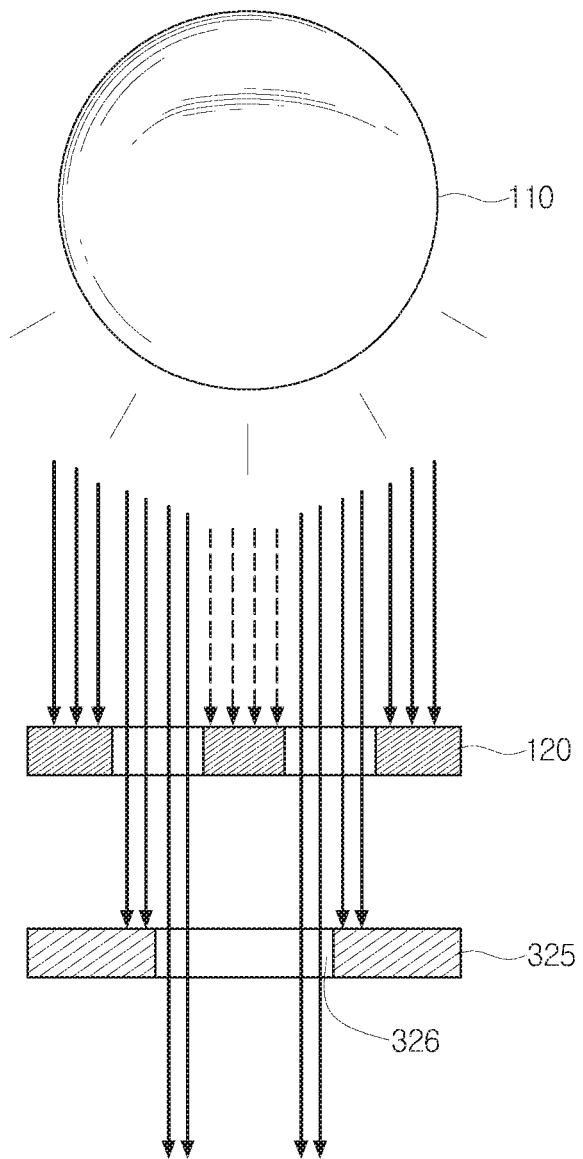
FIG. 11 is a view schematically illustrating a light emitted from a light source of a three-dimensional shape measurement apparatus capable of measuring color information of FIG. 10 penetrating a light adjuster.

FIG. 10 is a light path view schematically illustrating a three-dimensional shape measurement apparatus capable of measuring color information according to the third embodiment of the present disclosure, and FIG. 11 is a view which schematically illustrates that a light emitted from the light source of the three-dimensional shape measurement apparatus of FIG. 10 capable of measuring color information penetrates the light adjuster.

Referring to FIG. 10 or FIG. 11, the three-dimensional shape measurement apparatus capable of measuring color information according to the third embodiment of the present disclosure 300 is for adjusting a light entering the measurement object according to a magnification ratio of the lens unit 140. The three-dimensional shape measurement apparatus capable of measuring color information according to the third embodiment of the present disclosure 300 includes a light source 110, a light adjuster 120, a subsidiary light adjuster 325, a light divider 130, a lens unit 140, a second optical light divider 250, and a light detector 260.

The light source 110, the light adjuster 120, and the light divider 130 are the same as those in the first embodiment 100 of the present disclosure, and thus detailed explanation is omitted herein.

Furthermore, the second light divider 250 and light detector 260 are the same as those in the second embodiment 200 of the present disclosure, and thus detailed explanation is omitted herein.

The subsidiary light adjuster 325 is arranged on the light path between the light adjuster 120 and light divider 130, and the subsidiary light adjuster 325 additionally interrupts a partial area of the surrounding light that penetrates the light adjuster 325 according to a magnification ratio change of the lens unit 140 to adjust the area of light entering the measurement object. An aperture 326 where the light can penetrate is formed inside the subsidiary light adjuster 325.

That is, regarding the surrounding light that penetrated the light adjuster 120, only some of the surrounding light that penetrate the aperture 326 proceeds toward the light divider 130, thereby reducing the area of light entering the measurement object compared to when using only the light adjuster 120.

Herein, it is desirable that the aperture 326 is arranged to have the same central axis as the transmitter 122.

Furthermore, it is desirable that the aperture 326 is arranged to have a smaller size area than the transmitter 122 so as to additionally interrupt some of the surrounding light penetrating the light adjuster 120.

Herein, the aperture 326 may be formed to have at least one of a circular, a polygonal and a rod shape, but not limited to these shapes.

The light divider 130 performs the same function as the first embodiment 100 of the present disclosure, but the difference is that the light divider of the first embodiment 100 transmits or penetrates the surrounding light, whereas the light divider of the third embodiment 300 transmits or penetrates some of the surrounding light that penetrated the subsidiary light adjuster 325.

Hereinafter, explanation on an operation of the three-dimensional shape measurement apparatus capable of measuring color information according to the third embodiment of the present disclosure aforementioned will be made with reference to the light path.

The operation of the three-dimensional shape measurement apparatus capable of measuring color information according to the third embodiment of the present disclosure is the same as in the first embodiment 100 and second embodiment 200, and thus detailed explanation is omitted herein.

However, there is a difference that the subsidiary light adjuster 325 is arranged on the light path between the light adjuster 120 and light divider 130, and that regarding the surrounding light that penetrated the light adjuster 120, some of the surrounding light that penetrated the aperture 326 can proceed toward the light divider 130.

That is, when using the three-dimensional shape measurement apparatus, it is necessary to set the magnification ratio differently in consideration of the size or measurement precision of the measurement object, and when the magnification ratio of the three-dimensional shape measurement object is changed, it is necessary to further limit the area of the light entering the measurement object, and in the third embodiment 300, the color information of the measurement object is measured utilizing only some of the surrounding light according to the magnification ratio.

The scope of the present disclosure is not limited to the aforementioned embodiments, but may be realized in various formats of the embodiments within the range of the attached claims. It will be apparent to one of ordinary skill in the art that various changes in form and details may be made in these examples without departing from the spirit and scope of the claims.

INDUSTRIAL FEASABILITY

There is provided a three-dimensional shape measurement apparatus capable of measuring a shape of a measurement object using an interferometer and additionally measuring color information of the measurement object.

What is claimed is:
1. A three-dimensional shape measurement apparatus for measuring a shape of a measurement object using an interference light, the apparatus comprising:
   a light source for emitting light;
   a light divider for reflecting the light emitted from the light source or transmitting a light reflected by the measurement object;
   a lens unit for focusing the light reflected by the light divider onto the measurement object;
   a light detector for detecting the light reflected from the measurement object;
   a light adjuster arranged on a light path between the light source and the light divider and configured to interrupt the light being emitted from a central area of the light source to reduce interference of light occurring in the lens unit; and
   a subsidiary light adjuster arranged on the light path between the light adjuster and light divider and configured to interrupt a part of the light that penetrated the light adjuster to adjust the light entering the measurement object according to a magnification ratio of the lens unit;
   wherein the light adjuster comprises a main body provided with a transmitter for transmitting light, and a light diaphragm arranged inside the transmitter and configured to interrupt light;

wherein the light path where the light emitted from the light source penetrates is limited to an area between an exterior surface of the transmitter and an exterior surface of the light diaphragm, so as to reduce the light that is emitted from the central area of the light source and enters the measurement object;

wherein the subsidiary light adjuster is provided with an aperture for transmitting light, and wherein the aperture has a same central axis as the transmitter of the light adjuster and the aperture has a smaller outer diameter than the transmitter of the light adjuster such that a portion of surrounding light that penetrated the light adjuster is additionally interrupted.

2. The three-dimensional shape measurement apparatus according to claim 1, wherein the light detector comprises a first camera to be used in measuring the interference light and a second camera to be used in measuring color information, and further comprising a second light divider arranged on a light path between the light detector and the light divider and configured to transmit the light reflected from the measurement object to at least one of the first camera and the second camera.

3. The three-dimensional shape measurement apparatus according to claim 1, wherein the light diaphragm is formed to have at least one of a circular, a polygonal, and a rod shape.

\* \* \* \* \*